United States Patent
Pruche et al.

(10) Patent No.: US 8,084,268 B2
(45) Date of Patent: Dec. 27, 2011

(54) METHOD OF EVALUATING THE POTENTIAL OF THE SKIN FOR SCAVENGING FREE RADICALS

(75) Inventors: Francis Pruche, Senlis (FR); Quang Lan Nguyen, Antony (FR); Jean-Pascal Hirt, Saint-Cloud (FR)

(73) Assignee: L'Oreal, Paris (FR)

( * ) Notice: Subject to any disclaimer, the term of this patent is extended or adjusted under 35 U.S.C. 154(b) by 860 days.

(21) Appl. No.: 11/362,053

(22) Filed: Feb. 27, 2006

(65) Prior Publication Data

US 2006/0194333 A1 Aug. 31, 2006

Related U.S. Application Data

(60) Provisional application No. 60/665,388, filed on Mar. 28, 2005.

(30) Foreign Application Priority Data

Feb. 25, 2005 (FR) ...................................... 05 50525

(51) Int. Cl.
| | |
|---|---|
| G01N 31/22 | (2006.01) |
| A61B 5/00 | (2006.01) |
| A61K 49/00 | (2006.01) |
| A61K 39/395 | (2006.01) |
| C12Q 1/26 | (2006.01) |
| G01N 33/52 | (2006.01) |

(52) U.S. Cl. .............. 436/169; 424/9; 424/63; 424/130; 424/401; 435/7; 435/29; 435/405; 600/300; 600/301; 600/306; 600/309; 600/340; 600/362; 600/556; 600/557; 604/358; 604/362

(58) Field of Classification Search ........................ None
See application file for complete search history.

(56) References Cited

U.S. PATENT DOCUMENTS

| | | | |
|---|---|---|---|
| 4,595,011 A | 6/1986 | Phillips | |
| 5,667,501 A | 9/1997 | Fowler et al. | |
| 6,093,409 A | 7/2000 | Nadaud et al. | |
| 6,108,570 A | 8/2000 | Kohen et al. | |
| 6,316,012 B1 | 11/2001 | N'Guyen et al. | |
| 2003/0108542 A1* | 6/2003 | Pruche et al. ............. | 424/130.1 |

FOREIGN PATENT DOCUMENTS

EP    1 262 559 A1    12/2002

OTHER PUBLICATIONS

Groussard et al., "Free Radical Scavenging and Antioxidant Effects of Lactate ion: an In Vitro Study", Journal of Applied Physiology, vol. 89, pp. 169-175 (2000).*
J. Fuch et al; "HPLC Analysis of Vitamin E Isoforms in Human Epidermis: Correlation With Minimal Erythema Dose and Free Radical Scavenging Activity"; Free Radical Biology & Medicine, vol. 34; 2003; pp. 330-336; XP-002348232.

(Continued)

Primary Examiner — Krishnan S Menon
Assistant Examiner — Dirk Bass
(74) Attorney, Agent, or Firm — Oliff & Berridge, PLC

(57) ABSTRACT

A substrate is filled with a reagent that presents a stable free radical character, and that is capable of producing a visible reaction in the presence of at least one free radical scavenger analyte of the skin.

20 Claims, 3 Drawing Sheets

OTHER PUBLICATIONS

J. J. Thiele et al.; "Sebaceous Gland Secretion Is a Major Physiologic Route of Vitamin E Delivery to Skin"; The Society for Investigative Dermatology; Inc.; 1999; pp. 1006-1010.

Swarna Ekanayake Mudiyanselage et al.; "Ultraviolet A Induces Generation of Squalene Monohydroperoxide Isomers in Human Sebum and Skin Surface Lipids in Vitro and in Vivo"; The Society for Investigative Dermatology, Inc., 2003; pp. 915-922.

Phillippe Mondon et al.; "Evaluation of Free-Radical Scavenger Effects of *Helianthus annuus* Extract Using New Ex Vivo Stripping Methods"; Cosmetics, Aerosols & Toletries in Australia; pp. 1-15.

Office Action for European Patent Application No. 06 300 162.2-2404, dated Sep. 9, 2009 (w/English-language Translation).

\* cited by examiner

METHOD OF EVALUATING THE POTENTIAL OF THE SKIN FOR SCAVENGING FREE RADICALS

CROSS-REFERENCE TO RELATED APPLICATIONS

This non provisional application claims the benefit of French Application No. 05 50525 filed on Feb. 25, 2005, and U.S. Provisional Application No. 60/665,388 filed on Mar. 28, 2005, the entire disclosures of which are incorporated herein by reference.

BACKGROUND

The present invention relates to methods and devices that make it possible to evaluate the potential of the skin, including the lips, for scavenging free radicals, said potential also being referred to as "antioxidant potential."

Harmful free radicals are molecules that have a very short half-life, in the range 1 nanosecond (ns) to 1 millisecond (ms), and that are therefore very unstable and very reactive.

It is known that the ability of the skin to protect itself from external aggression such as exposure to ultraviolet rays, pollution, or other types of biological or chemical aggression, can depend in particular on its epidermal content of non-enzymatic antioxidants that are capable of scavenging the free radicals.

Thus, vitamin E is a known antioxidant for protecting the skin and for preventing it from aging, and it is often found in cosmetic formulations.

Depending on the individual, the concentration in the skin of antioxidants such as molecules with a thiol group, ascorbate, tocopherol, tocotrienol, uric acid, vitamin A, ubiquinone 10, spermine, and the like can vary, e.g. depending on age, skin type, diet, degree of exposure to ultraviolet rays, etc.

At present, common apparatus for monitoring free radicals directly is exceedingly expensive.

It has been proposed to use neutral sensor molecules called spin-trap that react to give radical-like molecules that are more stable and thus measurable by Electron Spin Resonance (ESR).

The formation of lipid peroxides or of squalene peroxides as indicators of cutaneous stress has been studied in the publication "Ultraviolet A induces generation of squalene monohydroperoxide isomers in human sebum and skin surface lipids in vitro and in vivo": S. E. Mudiyanselage, M. Hamburger, P. Elsner, J. J. Thiele, J. Invest. Dermatol. June 2003; 120(6) 915-22, and in German patent application DE 10 164 553.

The article "Evaluation of free radical scavenger effects of *Helianthus annus* extract using new ex vivo stripping methods," P. Mondon and al. in "Cosmetics, aerosols & toiletries" in Australia May 20, 1999, describes a method consisting in taking a sample of the *stratum corneum*, and in extracting therefrom the antioxidants the reaction of which with a colored reagent that is 1,1-Diphenyl-2-Picryl-Hydrazyl (DPPH) is carried, the bleaching of the reagent being monitored using a spectrophotometer at 517 nanometers (nm).

DPPH is a stable free radical, which, in the presence of one or more radical scavengers, loses its free radical character with a reduction in its color.

As a result of its stable character, DPPH has also been used in Electron Paramagnetic Resonance (EPR) techniques for measuring the free radical scavenger activity of the human epidermis, as described in the article "HPLC analysis of vitamin E isoforms in human epidermis: Correlation with minimal erythema dose and free radical scavenger activity": J. Fuchs, S. Weber, M. Podda, N. Groth, T. Herrling, L. Packer, R. Kaufmann, Free radic. Biol. Med. Feb. 1, 2003; 34 (3): 330-6.

Current analysis techniques implementing DPPH remain relatively complex and costly.

SUMMARY

Consequently, there is a need to benefit from means that make it possible to evaluate easily the antioxidant potential of the skin, e.g. with a view to determining whether the skin has sufficient resources of free radical scavenger substances, and whether an additional supply of antioxidants might be desirable.

The invention may obviate that need.

In one of its aspects, the invention provides a method of evaluating the free radical scavenger potential of the skin, the method comprising:

taking, in a manner that is not invasive to the skin, at least one sample of a free radical scavenger analyte that is present on the surface of the skin; and enabling the analyte taken in this way to react in contact with a reagent that is present on a substrate, and that is capable of producing a visible reaction in the presence of the analyte.

The invention tends towards a relatively high concentration of analytes and of reagents due to the fact that said analytes and reagents can be present in a thin layer when they are put into contact, thereby making it easier to detect a change in color.

The substrate may be applied directly on the skin's area comprising the analytes to be taken.

The change in color may be detected visually and/or by means of a device, e.g. a chromameter, or it may be detected in some other way, in particular by means of a scanner.

Where appropriate, a colorimetric scale may be used so as to make it easier to detect the change in color visually.

The invention may thus make it possible to benefit from means for evaluating the free radical scavenger potential of the skin that are simple to implement.

By way of example, taking a sample entails dissolving one or more free radical scavenger analytes that are present on the surface of the skin with a sampler liquid in which the reagent is preferably soluble, e.g. a liquid containing alcohol, in particular an ethanol solution.

The sampler liquid may impregnate a porous support, at least when taking a sample, thereby simplifying the sampling operation, and, where appropriate, the packaging of the liquid. By way of example, the porous support may be a support comprising fibers, with said support being cotton, for example.

By way of example, the support may be mounted at the end of a tube. Where appropriate, said tube may be hollow and may contain the sampler liquid.

The above-mentioned substrate carrying the reagent may be different from the porous support.

In particular, the substrate may be a membrane, and said membrane may be porous, preferably with porosity lying in the range 0.4 micrometers ($\mu m$) to 0.5 $\mu m$, e.g. about 0.45 $\mu m$.

The reagent-filled substrate is preferably dry. In a variant, the reagent-filled substrate is packaged in a damp state, the substrate being impregnated with the sampler liquid, for example.

By way of example, the material of the substrate is selected from polyamide, cellulose, cellulose acetate, polytetrafluoroethylene, polycarbonate, polyethersulfone, and polyvinylidene fluoride.

The concentration of reagent on the substrate lies in the range 0.2 milligrams (mg) to 20 mg per 100 square centimeters ($cm^2$), for example, and is preferably about 2 mg/100 $cm^2$, in particular when the substrate is a porous membrane.

By way of example, the reagent may comprise DPPH or any other appropriate reagent, in particular a reagent that presents a stable free radical character, and that is capable of producing a visible reaction in the presence of a free radical scavenger substance.

The substrate is preferably filled positively.

The reagent may be deposited on the substrate by spraying, silk-screen printing, ink-jet printing or impregnation, and where appropriate, it may be subjected to drying to a greater or lesser extent.

Before taking a sample, an outline of the area from which the sample is to be taken from the skin is defined, so as to treat a predefined area of skin while sampling, thereby improving the precision of the evaluation, and thereby making it easier to compare results.

By way of example, the outline of the sampling area is defined by applying a mask to the skin, in particular an adhesive mask, e.g. the mask being a sheet of paper that is coated on one face with an adhesive enabling it to be repositioned.

By way of example, such a mask includes a window having predefined dimensions.

When the sampler liquid is contained in a tube, said tube may present a scored end that is snapped off at the moment of use, so as enable the sampler liquid to flow to the porous support that is present at the other end of the tube.

In an exemplary embodiment of the invention, the porous support is used to collect the analyte(s) on the surface of the skin, in particular by being brought into contact therewith, while it is impregnated with the sampler liquid, and then the support is brought into contact with the reagent-filled substrate.

In another exemplary of embodiment of the invention, the sampler liquid is deposited on the skin, in particular by spraying, then the reagent-filled substrate is brought into contact therewith.

In still another example of embodiment of the invention, the reagent-filled substrate impregnated with sampler liquid is brought into contact with the skin.

In another of its aspects, the invention also provides a substrate filled with a reagent that presents a stable free radical character, and that is capable of producing a visible reaction in the presence of at least one free radical scavenger analyte of the skin.

The substrate may comprise a membrane, in particular a porous membrane, and, initially, the reagent may be colored.

The reagent comprises DPPH, for example.

The substrate may comprise a polymer material, in particular selected from polyamide, cellulose, cellulose acetate, polytetrafluoroethylene, polycarbonate, polyethersulfone, and polyvinylidene fluoride.

The substrate advantageously comprises solvents such as ethanol. The porosity of the substrate may make it easier for biological macromolecules to become attached. The substrate may include a fibrous matrix of a non-woven fabric, e.g. of polyester fibers, that imparts improved mechanical strength thereto. The fibrous matrix may be embedded in NYLON® 6,6, as with BIODYNE membranes from the supplier PALL.

The substrate may be dry.

The substrate may carry reagent only on its surface, or, in a variant, it may be filled more deeply with reagent, e.g. after being completely impregnated in the reagent.

The invention also provides a kit that makes it possible to evaluate the free radical scavenger potential of the skin, the kit including at least one substrate as defined above.

Advantageously, the kit includes a sampler element that makes it possible, in a manner that is not invasive to the skin, to take at least one sample of the free radical scavenger analyte that is present on the surface of the skin, with a view to causing it to react with the reagent.

The sampler element may be arranged so as to make it possible to package a sampler liquid before use. By way of example, the sampler element is thus in the form of a hollow tube that is filled with sampler liquid, and that is provided at one end with a score line, and at the other end with a porous support into which the sampler liquid may flow after the scored end has been snapped off.

The kit may further include a colorimetric scale, and means that make it possible to define an area of skin on which sampling is to take place, e.g. a mask, and in particular an adhesive mask.

In another of its aspects, the invention also provides a method of revealing the effect of an action on the free radical scavenger potential of the skin, in which method:

a) the free radical scavenger potential of the skin is determined, e.g. by implementing the method as defined above;

b) an action that is capable of acting on the potential is performed; and c) after said action, the potential is determined once again, and the incidence of said action on the potential is evaluated by comparing the results before and after the action.

By way of example, the action comprises applying a substance to the skin and/or ingesting at least one food supplement, or exposing the skin to a particular environment, e.g. the sun.

The effect of the ultraviolet rays on the free radical scavenger potential of the skin can thus be revealed, and the results can, for example, be used in an awareness campaign for making people aware of the effects of the sun, and/or they can be used for promoting the sale of substances that seek to reduce cutaneous stress associated with the sun.

Where appropriate, the above-mentioned kit may further include a substance for applying to the skin, e.g. a sun-screen or an anti-aging substance.

In one example of embodiment of the invention, the free radical scavenger potential of the skin is evaluated both before and after exposure to a source of cutaneous stress, e.g. the sun, both when the skin is not protected, and when the skin is protected, and the results are compared so as to reveal the protective effect of the substance applied to the skin.

The invention also provides a method in which the free radical scavenger potential of the skin is evaluated by implementing an evaluation method as defined above, and in which advice is then delivered relating to a substance and/or to a treatment that is intended to have an effect on the potential, as a function of the result of the evaluation.

The invention also provides a method of formulating a personalized cosmetic or dermatological composition, in which method the free radical scavenger potential of the skin of a person is evaluated, and, as a function of the potential determined in this way, the quantity of at least one antioxidant in the composition is determined for said person. By way of example, the antioxidant may be selected from: vitamin E, (alpha tocopherols and isomers), ascorbic acid, coenzyme Q, uric acid, carotenoids, flavonoids and polyphenols, aminoindoles and melatonin, and dihydrolipoic acid, etc. . . .

BRIEF DESCRIPTION OF THE DRAWINGS

The invention can be better understood on reading the following detailed description of non-limiting embodiments thereof, and on examining the accompanying drawings, in which.

DETAILED DESCRIPTION OF EMBODIMENTS

Figure 1:
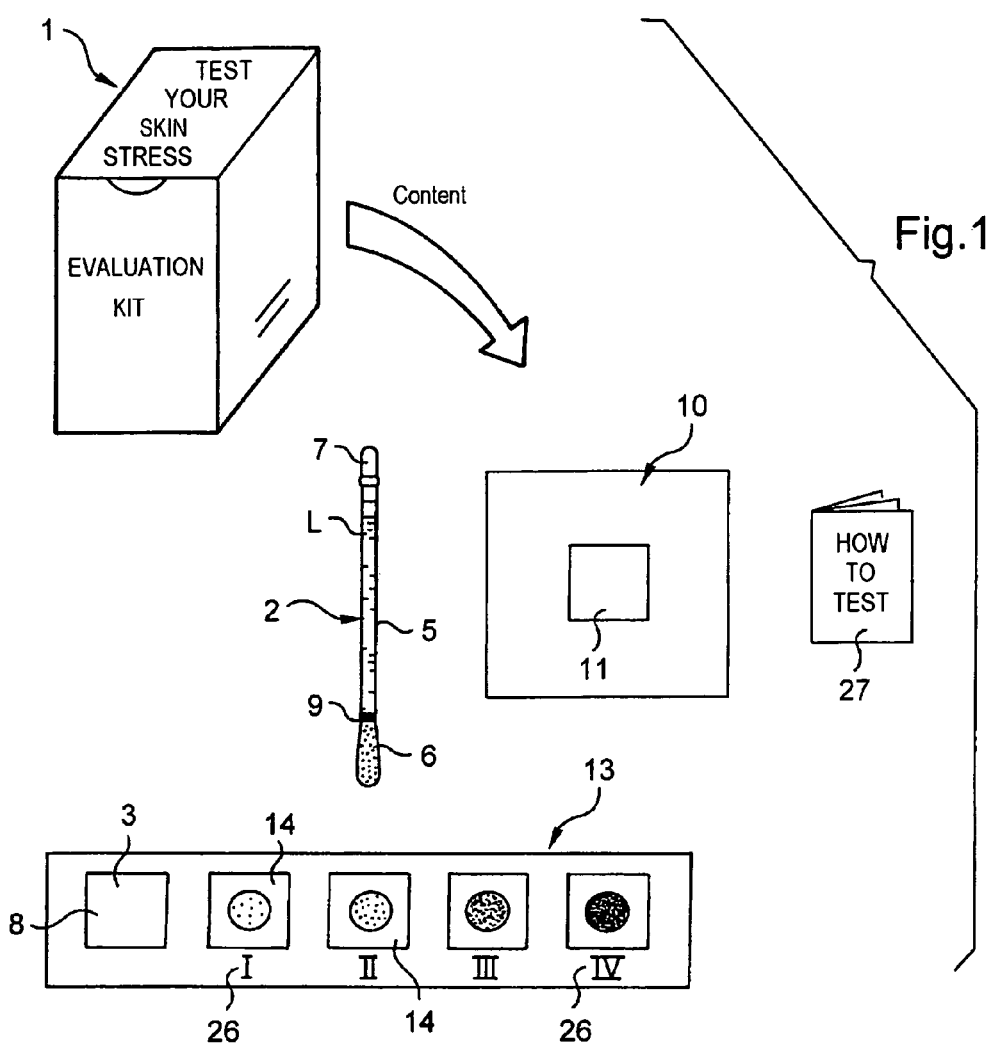
FIG. 1 is a diagrammatic perspective view of an example of a kit of the invention.

The kit 1 shown in FIG. 1 comprises a sampler element 2 for taking one or more samples of analytes from the surface of the skin, and a reagent 3 that makes it possible to produce a visible reaction in the presence of the analyte(s).

By way of example, the sampler element 2 comprises a tube 5 that is filled with a sampler liquid L, the tube 5 being provided at one end with a porous support 6, and at its other end with a scored portion 7. When said scored portion is snapped off, air is sucked into the tube 5 above the liquid L, and said liquid can flow into the support 6.

Examples of suitable sampler elements are described in U.S. patent application No. 2004/0158188, and said elements can be obtained from the American supplier SWAB PLUS.

In the tube 5 above the support 6, the sampler element 2 can include a plug 9 of liquid that does not mix with the sampler liquid, so as to isolate the sampler liquid L from the outside. By way of example, the plug 9 is a meniscus of silicone oil that is capable of being expelled with the sampler liquid L when said sampler liquid leaves the tube 5.

By way of example, the support 6 is a cotton tip or "bud."

By way of example, the sampler liquid L is a 10% ethanol solution.

By way of example, the reagent 3 is DPPH that is deposited on a substrate 8 that is selected so that it does not affect the reactivity of the reagent, and that is preferably porous so as to make it easier for the reagent to impregnate it.

In the embodiment under consideration, the substrate 8 is a membrane that withstands organic solvents such as ethanol, it does not contain any traces of peroxides that could decrease the sensitivity of the reagent to the antioxidants, and it does not contain antioxidants that could reduce the reagent and affect detection.

By way of example, the substrate 8 is a polyamide membrane, e.g. a NYLON® 6,6 membrane that has been filled positively. The membrane presents a porous surface with a pore size of 0.2 µm, 0.45 µm, or 1.2 µm, for example, and preferably 0.45 µm.

By way of example, the thickness of the membrane is 6 millimeters (mm), more or less 0.5 mm.

Suitable membranes are sold by the American company PALL CORPORATION under the trade names BIODYNE B or C.

By way of example, the membrane 8 can be in the form of an independent pastille, or, as in the embodiment shown, it can be disposed beside reference color indicators 14 making up a colorimetric scale 13, making it possible to evaluate more easily a color change in said membrane.

By way of example, the color indicators 14 are associated with alpha-numerical or other identifiers 26, making it possible to identify them.

The kit 1 can include instructions 27 informing the user of the kit 1 on how to conduct the test, and on the analysis that is required to obtain the results of the evaluation, e.g. as a function of the identifier 26 corresponding to the observed change in color.

In one example of embodiment of the invention, the membrane 8 is in the form of a 2 centimeter (cm)×2 cm square pastille made from a 10 cm×10 cm sheet of BIODYNE B or C that has already been filled with reagent 3 by depositing 2 milliliters (mL) of a DPPH solution from the German supplier SIGMA ALDRICH CHEMIE, STEINHEIN, at a concentration of 100 mg/100 mL of 96% ethanol, then it is agitated, and oven dried at normal temperature for two hours.

The concentration of DPPH on the membrane lies in the range 0.2 mg to 20 mg per 100 $cm^2$, for example, and is preferably about 2 mg/100 $cm^2$.

In the embodiment under consideration, the kit 1 also includes a mask 10, e.g. made of paper of the POST IT® type, having a face that is coated with a pressure-sensitive adhesive. The mask 10 has a window 11 passing therethrough.

Figure 2:
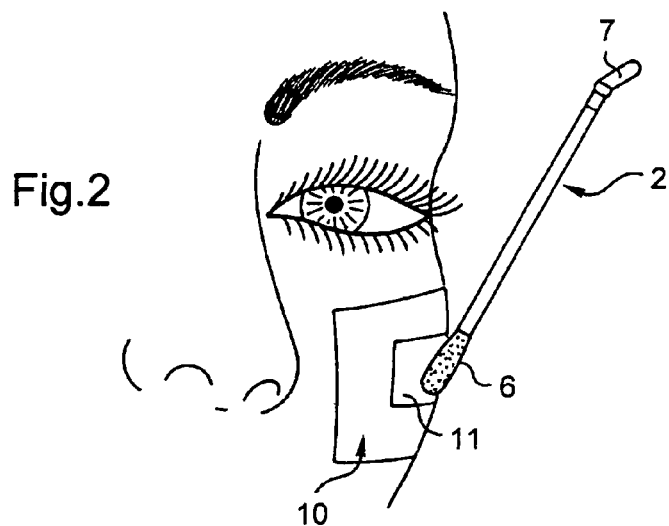
FIGS. 2 and 3 show the kit in use.

In use, the mask 10 is applied to the area in which the sampling is to be taken, e.g. the face in the example in FIG. 2.

The scored end 7 is snapped off and the sampler liquid L flows into the support 6. The support 6 is brought in contact with the area of skin defined by the window 11, and the analytes present on the surface of said area of skin are taken, e.g. by brushing the support 6 horizontally then vertically over the sampling area.

Figure 3:
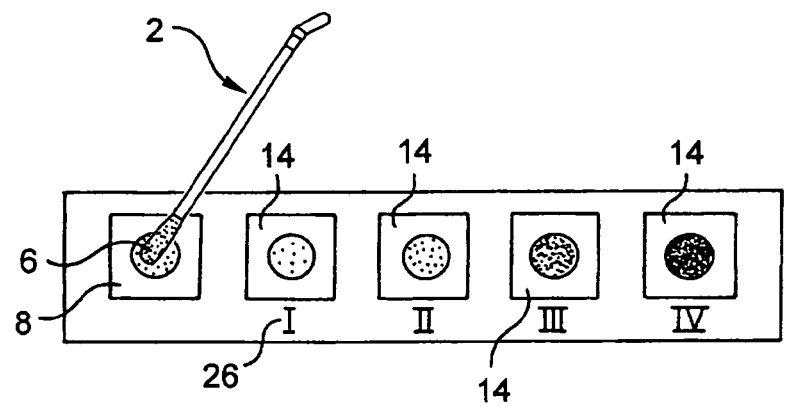

Then, the support 6 is brought into contact, e.g. for 10 seconds, with the substrate 8 filled with the reagent 3, as shown in FIG. 3.

In the presence of a 10% ethanol solution, the substrate 8 is red/pink, for example. In the presence of a lipophilic antioxidant such as vitamin E, for example, bleaching is observed, said bleaching being proportional to the quantity of vitamin E. The observed bleaching can be evaluated by comparing it with the color indicators 14, after a predefined period of time, e.g. 60 seconds (s) to 120 s.

Evaluating the free radical scavenger potential of the skin can be useful, e.g. for revealing the need for a treatment, or the effect of a treatment on the skin.

By way of example, the kit 1 is used at a point of sale, in a beauty institute, or by a dermatologist, so as to advise a consumer or a patient on the possible need for a treatment. In this event, one or more substances for applying to the skin, or for ingesting, can be recommended after seeing the result of the evaluation.

By way of example, substance(s) to be ingested can comprise more than 50 mg or vitamin C, more than 5 mg of vitamin E, more than 100 mg of grape or tea polyphenols, more than 1 µg of selenium, and/or more than 1 mg of betacarotene.

By way of example, it is possible to propose an oral formulation corresponding to a daily dose of 60 mg of vitamin C, 10 mg of vitamin E, 200 mg of grape or tea polyphenols, 2 µg of selenium, and 2 mg of betacarotene.

The kit can also be used at the consumer's home. In this event, the consumer can take the sample, and can then detect a change in color in the reagent.

Regardless of whether or not the evaluation is performed at home, a device can be used to make it easier to detect a change in the color of the reagent.

Measuring absorption at a predefined wavelength, e.g. 517 nm, makes it possible to detect a variation in the color of the reagent, for example. A chromameter can also be used.

Figure 4:
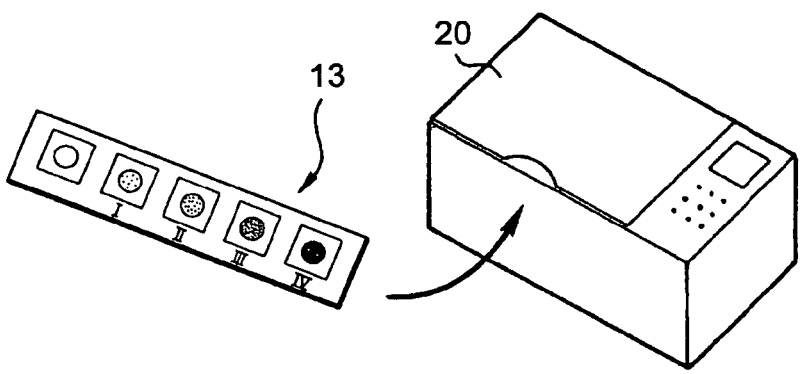
FIG. 4 shows the use of a device for detecting a change in color.

In one example of embodiment of the invention, the color of the substrate 8 is compared with the color of the color indicators 14 by means of a color scanner 20, said scanner being integrated in a multifunction color printer, for example, as shown in FIG. 4.

The printer can be connected to a micro-computer or to a mobile terminal, not shown, that is responsible for analyzing the image digitized in this way, so as to detect the change in color.

Figure 5:
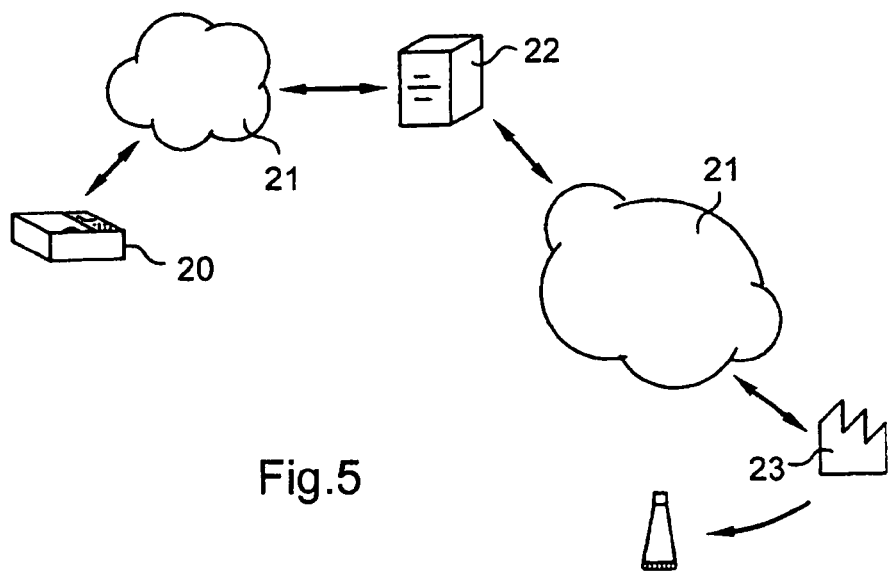
FIG. 5 shows the remote processing of data resulting from the evaluation of the free radical scavenger potential.

The scanner can also be connected, directly or otherwise, to a computer network 21, e.g. Internet, and it can download a program from the network 21 for performing the comparison, as shown in FIG. 5.

Where appropriate, the data processing can be performed by a remote server 22, to which the digitized image is transmitted, for example.

The server 22 can then transmit information to the consumer, in particular an analysis result, which can be accompanied by the prescription of a substance, indeed by the supply of a personalized substance, with the server 22 using the network 2, for example, to communicate information to a manufacturing center 23.

By way of example, the personalized substance comprises an antioxidant at a concentration that is a function of the previously evaluated free radical scavenger potential of the skin.

By way of example, the substance is selected from vitamin E, vitamin C, NDGA, thiols and derivatives thereof (Glutathione, N-acetylcysteine), procyanidolic oligomers (OPC), flavonoids, catechins, epicatechins and gallic acid derivatives thereof, polyphenols such as tyrosol, hydroxytyrosol, sesamol, carnosol, gamma oryzanol, for example, acids such as ferulic acid, caffeic acid, rosemarinic acid, carnosic acid, etc.

The invention can also be implemented to evaluate the effect of a treatment on the skin.

Figure 6:
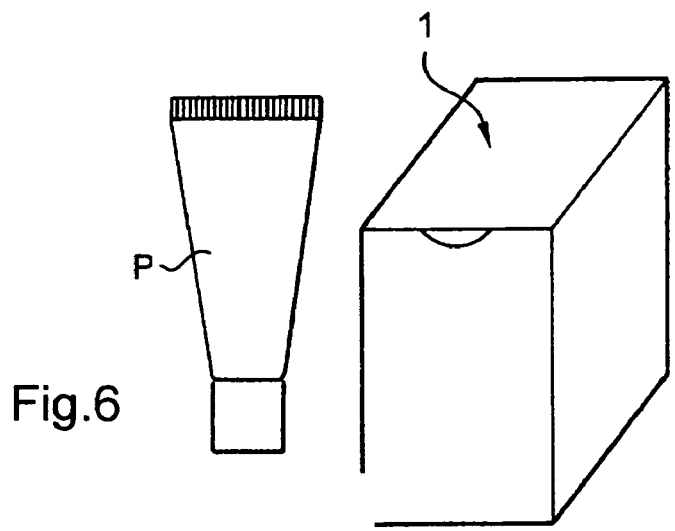
FIG. 6 shows a set comprising the FIG. 1 kit and an associated substance.

By way of example, the kit 1 is proposed as an accompaniment to the substance P for applying to the skin, with said kit being sold together with the substance, for example, as shown in FIG. 6.

By way of example, the user can evaluate the free radical scavenger potential of the skin before using the substance, and then after using the substance, and, by comparing the results, can determine the effect of the treatment on the potential.

The evaluation kit can also be used so as to determine the dosage for a substance having an effect on the antioxidant potential of the skin, e.g. the number of applications of the substance per time interval, or the quantity to be applied.

The evaluation kit 1 can also be used to determine the regions of the body to be treated, e.g. by showing that some regions of the body have a free radical scavenger potential that is higher than others, said others consequently having a greater need for treatment.

The invention can also be useful in revealing the effect of an environment on the skin, e.g. in evaluating the cutaneous stress resulting from exposure to the sun.

Two regions of the body, respectively exposed and unexposed to the sun, can be evaluated, and the results compared. Such a comparison can reveal the cutaneous stress that is generated to a greater or lesser extent by the sun, depending on the individual.

An identifier that is determined while evaluating the free radical scavenger potential of the skin, or while evaluating the ability of the skin to withstand cutaneous stress, can appear on substances or in correspondence tables associated with substances, so as to enable users who are aware of the antioxidant potential of their own skin, or of the ability of their own skin to withstand stress from a free radical generator, to select suitable substances.

The use of a membrane to convey the reagent 3 constitutes only one example of a substrate from amongst others.

Figure 7:
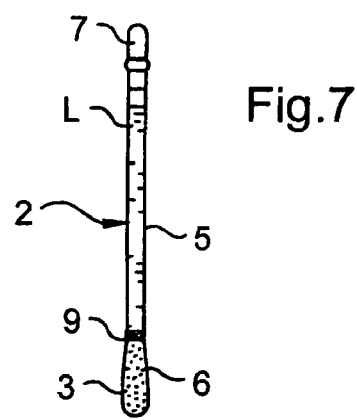
FIGS. 7 and 8 show two variant embodiments.

For example, the support 6 of the sampler element 2 can also be used as a substrate for the reagent, as shown in FIG. 7.

The sampler element 2 can thus be used as follows.

The scored end 7 is snapped off, thereby enabling the sampler liquid to soak into the support 6, then said support is brought into contact with the skin in order to collect analytes that are capable of reacting with the reagent 3.

A possible change in color is thus observed directly on the support 6.

Where appropriate, the support can be other than a cotton tip, so as to make it easier to detect the change in color visually.

Figure 8:
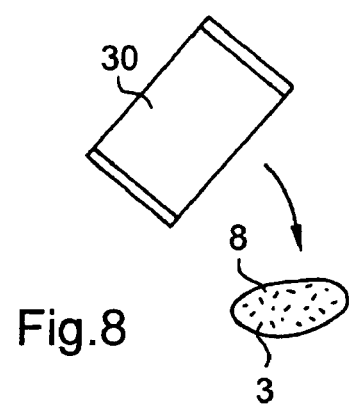

As shown in FIG. 8, the reagent 3 can also be present on a wipe, a pastille, or a patch, with such a substrate being pre-impregnated with the sampler liquid, and packaged in sealed manner in a sachet 30.

In order to use such a sampler element, the user extracts the substrate, which is also the support for the sampler liquid, from the sachet 30, and then applies the substrate to the skin in such a manner as to collect the analytes that are situated on its surface.

The color reaction is observed on the substrate.

In a variant, the sampler liquid can also be sprayed or deposited in some other way on the skin, then the reagent-filled substrate, and dry for example, is brought into contact therewith.

Naturally, the invention is not limited to the embodiments described above.

In particular, DPPH can be replaced by other suitable reagents, in particular markers having a radical that changes color by a free electron matching effect and having a half-life of about the same duration as DPPH, for example.

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

Throughout the description, including in the claims, the expression "comprising a" should be understood as being synonymous with the expression "comprising at least one," unless specified to the contrary.

What is claimed is:

1. A method of evaluating a free radical scavenger potential of skin, the method comprising:
   taking, in a manner that is not invasive to the skin, at least one sample of a free radical scavenger analyte that is present on the surface of the skin by collecting the analyte on the surface of the skin with a porous support;
   removing said porous support comprising said analyte from the surface of the skin; and then
   reacting the analyte taken in this way with a reagent that is present on a solid substrate by bringing the porous support into contact with the reagent-filled substrate, the substrate being separate from the porous support, wherein the reagent produces a visible reaction in the presence of the analyte, the reagent comprising DPPH, and the visible reaction being produced in 60 seconds to 120 seconds.

2. A method according to claim 1, wherein taking the sample entails dissolving the at least one analyte with a sampler liquid.

3. A method according to claim 2, wherein the reagent is soluble in the sampler liquid.

4. A method according to claim 2, wherein the sampler liquid comprises alcohol.

5. A method according to claim 4, wherein the sampler liquid comprises ethanol.

6. A method according to claim 1, wherein the sampler liquid impregnates the porous support, at least when taking the sample.

7. A method according to claim 6, wherein the porous support comprises fibers.

8. A method according to claim 6, wherein the porous support is disposed at an end of a tube.

9. A method according to claim 8, wherein the porous support is cotton.

10. A method according to claim 8, wherein the tube contains the sampler liquid.

11. A method according to claim 1, wherein the substrate is a membrane.

12. A method according to claim 1, wherein the substrate is porous.

13. A method according to claim 12, wherein the substrate is made out of a material selected from the group consisting of polyamide, cellulose, cellulose acetate, polytetrafluoroethylene, polycarbonate, polyethersulfone, and polyvinylidene fluoride.

14. A method according to claim 1, wherein a colorimetric scale is used when a change in color is visually detected in the reagent.

15. A method according to claim 1, wherein, before taking the sample, an outline of the area from which the sample is to be taken from the skin is defined.

16. A method according to claim 15, wherein said outline is defined by applying a mask to the skin.

17. A method according to claim 16, wherein the mask is adhesive.

18. A method according to claim 8, wherein the tube presents a scored end that is snapped off at the moment of use, so as to enable the sampler liquid to flow to the porous support.

19. A method for delivering a cosmetic advice, the method comprising:
  evaluating the free radical scavenger potential of skin of a person by implementing the method as defined in claim 1, and
  delivering an advice relating to a substance and/or to a treatment intended to have an effect on the potential.

20. A method of formulating a personalized cosmetic or dermatological composition, the method comprising:
  evaluating the free radical scavenger potential of skin of a person by implementing the method as defined in claim 1, and
  determining the quantity of at least one antioxidant in a composition determined for said person.

* * * * *